(12) United States Patent
Orinski et al.

(10) Patent No.: US 9,474,546 B1
(45) Date of Patent: Oct. 25, 2016

(54) PRE-CURVED ELECTRODE ARRAY INSERTION TOOLS

(75) Inventors: William G. Orinski, Stevenson Ranch, CA (US); Steve J. Blomquist, Tucson, AZ (US); Mark B. Downing, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 1258 days.

(21) Appl. No.: 12/425,868

(22) Filed: Apr. 17, 2009

Related U.S. Application Data

(60) Provisional application No. 61/046,302, filed on Apr. 18, 2008.

(51) Int. Cl.
| | | |
|---|---|---|
| A61N 1/05 | (2006.01) | |
| A61B 17/34 | (2006.01) | |
| A61B 17/00 | (2006.01) | |
| A61N 1/36 | (2006.01) | |

(52) U.S. Cl.
CPC .. *A61B 17/3468* (2013.01); *A61B 2017/00477* (2013.01); *A61N 1/0541* (2013.01); *A61N 1/36032* (2013.01)

(58) Field of Classification Search
CPC ............... A61B 17/3468; A61B 2017/0477; A61N 1/36032; A61N 1/0541
USPC .............. 606/129; 607/57, 137; 600/585
See application file for complete search history.

(56) References Cited

U.S. PATENT DOCUMENTS

| | | |
|---|---|---|
| 3,530,860 A | 9/1970 | Majoros |
| 3,973,560 A | 8/1976 | Emmett |
| 4,180,080 A | 12/1979 | Murphy |
| 4,280,510 A | 7/1981 | O'Neill |
| 4,488,561 A | 12/1984 | Doring |
| 4,532,930 A | 8/1985 | Crosby et al. |
| 4,646,755 A | 3/1987 | Kane |
| 4,665,918 A | 5/1987 | Garza et al. |
| 4,787,884 A | 11/1988 | Goldberg |
| 4,819,647 A | 4/1989 | Byers et al. |
| 4,865,037 A | 9/1989 | Chin et al. |

(Continued)

FOREIGN PATENT DOCUMENTS

| | | |
|---|---|---|
| EP | 0109304 | 5/1984 |
| EP | 0328597 | 8/1989 |

(Continued)

OTHER PUBLICATIONS

International Search Report and Written Opinion received in International Application No. PCT/US2007/083428, May 20, 2008.

(Continued)

*Primary Examiner* — Diane Yabut
(74) *Attorney, Agent, or Firm* — ALG Intellectual Property, LLC

(57) ABSTRACT

Exemplary insertion tools for facilitating insertion of an electrode array into a bodily orifice include a stylet assembly having a stylet configured to be inserted into a lumen of the electrode array, a slide assembly configured to at least partially house the stylet assembly, and a handle assembly configured to engage at least a portion of the slide assembly. The slide assembly may be configured to selectively disengage from the handle assembly. The stylet assembly may be configured to selectively disengage from the slide assembly while the stylet is still inserted into the lumen of the electrode array. Corresponding systems and methods are also described.

15 Claims, 12 Drawing Sheets

(56) References Cited

U.S. PATENT DOCUMENTS

| | | |
|---|---|---|
| 4,898,183 A | 2/1990 | Kuzma |
| 4,994,069 A | 2/1991 | Ritchart et al. |
| 5,046,497 A | 9/1991 | Millar |
| 5,110,529 A | 5/1992 | Arima |
| 5,117,839 A * | 6/1992 | Dance ............... A61M 25/0136 600/434 |
| 5,159,861 A | 11/1992 | Anderson |
| 5,312,415 A | 5/1994 | Palermo |
| 5,314,464 A | 5/1994 | KenKnight et al. |
| 5,443,493 A | 8/1995 | Byers et al. |
| 5,545,200 A | 8/1996 | West et al. |
| 5,545,219 A | 8/1996 | Kuzma |
| 5,558,673 A | 9/1996 | Edwards et al. |
| 5,579,780 A | 12/1996 | Zadini et al. |
| 5,645,585 A | 7/1997 | Kuzma |
| 5,667,514 A | 9/1997 | Heller |
| 5,749,371 A | 5/1998 | Zadini et al. |
| 5,810,852 A | 9/1998 | Greenberg et al. |
| 5,814,062 A | 9/1998 | Sepetka et al. |
| 5,902,331 A | 5/1999 | Bonner et al. |
| 5,906,619 A | 5/1999 | Olson et al. |
| 5,999,859 A | 12/1999 | Jolly |
| 6,070,105 A | 5/2000 | Kuzma |
| 6,071,282 A | 6/2000 | Fleischman |
| 6,078,841 A | 6/2000 | Kuzma |
| 6,093,197 A | 7/2000 | Bakula et al. |
| 6,119,044 A | 9/2000 | Kuzma |
| 6,125,302 A | 9/2000 | Kuzma |
| 6,129,753 A | 10/2000 | Kuzma |
| 6,149,657 A | 11/2000 | Kuzma |
| 6,163,729 A | 12/2000 | Kuzma |
| 6,195,586 B1 | 2/2001 | Kuzma |
| 6,208,882 B1 | 3/2001 | Lenarz et al. |
| 6,219,580 B1 | 4/2001 | Faltys et al. |
| 6,272,382 B1 | 8/2001 | Faltys et al. |
| 6,293,945 B1 | 9/2001 | Parins et al. |
| 6,304,785 B1 | 10/2001 | McCreery et al. |
| 6,308,101 B1 | 10/2001 | Faltys et al. |
| 6,312,429 B1 | 11/2001 | Burbank et al. |
| 6,321,125 B1 | 11/2001 | Kuzma |
| 6,421,569 B1 | 7/2002 | Treaba et al. |
| 6,500,130 B2 * | 12/2002 | Kinsella et al. ............. 600/585 |
| 6,547,762 B1 | 4/2003 | Botich et al. |
| 6,582,441 B1 | 6/2003 | He et al. |
| 6,604,283 B1 | 8/2003 | Kuzma |
| 6,746,412 B1 | 6/2004 | Hill et al. |
| 6,858,034 B1 | 2/2005 | Hijlkema et al. |
| 6,866,669 B2 | 3/2005 | Buzzard |
| 6,936,065 B2 | 8/2005 | Khan et al. |
| 6,939,352 B2 | 9/2005 | Buzzard |
| 6,968,238 B1 | 11/2005 | Kuzma |
| 7,050,858 B1 | 5/2006 | Kuzma et al. |
| 7,063,708 B2 | 6/2006 | Gibson et al. |
| 7,269,461 B2 | 9/2007 | Dadd et al. |
| 7,349,744 B2 | 3/2008 | Dadd et al. |
| 7,473,256 B2 * | 1/2009 | Assell et al. ............... 606/90 |
| 7,544,197 B2 | 6/2009 | Kelsch et al. |
| 7,591,268 B2 | 9/2009 | Lowe et al. |
| 7,792,586 B2 | 9/2010 | Dadd et al. |
| 7,966,077 B2 | 6/2011 | Risi |
| 2002/0045927 A1 | 4/2002 | Moore et al. |
| 2002/0143302 A1 | 10/2002 | Hinchliffe et al. |
| 2002/0147484 A1 | 10/2002 | Dahl |
| 2003/0045921 A1 | 3/2003 | Dadd et al. |
| 2003/0093139 A1 | 5/2003 | Gibson et al. |
| 2003/0171758 A1 | 9/2003 | Gibson et al. |
| 2004/0122312 A1 | 6/2004 | Chesbrough et al. |
| 2004/0127968 A1 | 7/2004 | Kuzma et al. |
| 2004/0193203 A1 | 9/2004 | Pak et al. |
| 2004/0220651 A1 | 11/2004 | Kuzma et al. |
| 2004/0243177 A1 | 12/2004 | Svehla et al. |
| 2004/0260371 A1 | 12/2004 | Greenland et al. |
| 2005/0004644 A1 | 1/2005 | Kelsch et al. |
| 2005/0075606 A1 | 4/2005 | Botich et al. |
| 2005/0251237 A1 | 11/2005 | Kuzma et al. |
| 2006/0058861 A1 | 3/2006 | Gibson et al. |
| 2006/0155353 A1 | 7/2006 | Heil, Jr. |
| 2006/0241723 A1 * | 10/2006 | Dadd et al. ............... 607/57 |
| 2007/0043419 A1 | 2/2007 | Nikolchev et al. |
| 2007/0111175 A1 | 5/2007 | Raven et al. |
| 2007/0213812 A1 | 9/2007 | Webler et al. |
| 2007/0233214 A1 | 10/2007 | Chitre et al. |
| 2008/0004684 A1 | 1/2008 | Dadd et al. |
| 2008/0082141 A1 | 4/2008 | Risi |
| 2008/0109011 A1 | 5/2008 | Thenuwara et al. |
| 2008/0195146 A1 | 8/2008 | Wardle |
| 2008/0269740 A1 | 10/2008 | Bonde et al. |
| 2008/0269763 A1 | 10/2008 | Bonde et al. |
| 2009/0119920 A1 | 5/2009 | Peschke et al. |
| 2011/0009877 A1 | 1/2011 | Thenuwara et al. |
| 2011/0301681 A1 | 12/2011 | Risi |

FOREIGN PATENT DOCUMENTS

| | | |
|---|---|---|
| EP | 1233810 | 8/2002 |
| EP | 1341578 | 9/2003 |
| EP | 1370205 | 12/2003 |
| EP | 1476104 | 11/2004 |
| EP | 2039323 | 3/2009 |
| WO | WO-80/02231 | 10/1980 |
| WO | WO-8900870 | 2/1989 |
| WO | WO-9324058 | 12/1993 |
| WO | WO-95/11710 | 5/1995 |
| WO | WO-9720530 | 6/1997 |
| WO | WO-00/64529 | 11/2000 |
| WO | WO-00/71063 | 11/2000 |
| WO | WO-01/068177 | 9/2001 |
| WO | WO-02/30507 | 4/2002 |
| WO | WO-0230507 | 4/2002 |
| WO | WO-0232498 | 4/2002 |
| WO | WO-02074211 | 9/2002 |
| WO | WO-03/070133 | 8/2003 |
| WO | WO-03070133 | 8/2003 |
| WO | WO 2004/014472 | 2/2004 |
| WO | WO-2004012809 | 2/2004 |
| WO | WO-2005/110529 | 11/2005 |
| WO | WO-2010/045228 A3 | 4/2010 |
| WO | WO-2010/133704 A2 | 11/2010 |
| WO | WO-2011/005993 A1 | 1/2011 |

OTHER PUBLICATIONS

International Search Report and Written Opinion received in International Application No. PCT/US2011/041576, dated Sep. 19, 2011.

International Search Report and Written Opinion received in International Application No. PCT/US2011/041577, dated Nov. 30, 2011.

Non-Final Office Action received in U.S. Appl. No. 12/824,119, dated Jun. 8, 2012.

Non-Final Office Action received in U.S. Appl. No. 12/824,120, dated Jun. 8, 2012.

Final Office Action received in U.S. Appl. No. 12/824,122, dated Sep. 6, 2013.

Final Office Action received in U.S. Appl. No. 12/824,120, dated Oct. 1, 2013.

Final Office Action received in U.S. Appl. No. 12/824,119, dated Oct. 4, 2013.

Final Office Action received in U.S. Appl. No. 12/824,122 dated Dec. 2, 2013.

* cited by examiner

PRE-CURVED ELECTRODE ARRAY INSERTION TOOLS

RELATED APPLICATIONS

The present application claims priority under 35 U.S.C. §119(e) to U.S. Provisional Patent Application No. 61/046,302 by William G. Orinski et al., filed on Apr. 18, 2008, and entitled "Pre-curved Electrode Array Insertion Tools," the contents of which are hereby incorporated by reference in their entirety.

BACKGROUND

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, an array of electrodes may be implanted in the cochlea. The electrodes form a number of stimulation channels through which electrical stimulation pulses may be applied directly to auditory nerves within the cochlea. An audio signal may then be presented to a patient by translating the audio signal into a number of electrical stimulation pulses and applying the stimulation pulses directly to auditory nerves within the cochlea via one or more of the electrodes.

The electrode array is often implanted within the scala tympani, one of the three parallel ducts that make up the spiral-shaped cochlea. Electrode arrays that are implanted in the scala tympani typically include a thin, elongate, and flexible carrier containing several longitudinally disposed and separately connected stimulating electrode contacts. Such an electrode array is pushed into the scala tympani duct to a depth of about 18-25 mm via a surgical opening made in the cochlea wall at or near the round window at the basal end of the duct.

During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one electrode contact site tends to selectively activate those spiral ganglion cells and their auditory nerve fibers that are closest to that contact site.

Hence, it is often desirable for the electrode contacts to be positioned as close to the ganglion cells as possible and/or to any other location (e.g., a mid-scalar location) as may serve a particular application. To this end, various pre-curved electrode arrays have been developed that have spiral-shaped resilient carriers to better conform to the shape of the scala tympani and/or other auditory structures.

Pre-curved electrode arrays generally have to first be loaded onto a straight stylet before they can be inserted into the cochlea. In many cases, a pre-curved electrode array comes preloaded on a stylet that is a component of an insertion tool used to facilitate the implantation of the electrode array in the cochlea. However, some practitioners find the insertion tools cumbersome and would prefer to implant the electrode array using only the stylet component.

SUMMARY

Exemplary insertion tools for facilitating insertion of an electrode array into a bodily orifice include a stylet assembly having a stylet configured to be inserted into a lumen of the electrode array, a slide assembly configured to at least partially house the stylet assembly, and a handle assembly configured to engage at least a portion of the slide assembly. The slide assembly may be configured to selectively disengage from the handle assembly. The stylet assembly may be configured to selectively disengage from the slide assembly while the stylet is still inserted into the lumen of the electrode array.

Exemplary systems include a pre-curved electrode array configured to provide electrical stimulation to one or more stimulation sites within a duct of a cochlea and an insertion tool configured to insert the electrode array into the duct of the cochlea. The insertion tool includes a stylet assembly comprising a stylet configured to be inserted into a lumen of the electrode array, a slide assembly configured to at least partially house the stylet assembly, and a handle assembly configured to engage at least a portion of the slide assembly. The slide assembly may be configured to selectively disengage from the handle assembly. The stylet assembly may be configured to selectively disengage from the slide assembly while the stylet is still inserted into the lumen of the electrode array.

Exemplary methods of inserting a pre-curved electrode array into a bodily orifice include inserting a stylet of a stylet assembly into a lumen of a pre-curved electrode array, providing a slide assembly configured to at least partially house the stylet assembly, providing a handle assembly configured to engage at least a portion of the slide assembly, disengaging the handle assembly from the slide assembly, disengaging the stylet assembly from the slide assembly while the stylet is still inserted into the lumen of the pre-curved electrode array, and using the stylet assembly to insert the pre-curved electrode array into the bodily orifice.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Exemplary insertion tools for facilitating insertion of an electrode array into a bodily orifice are described herein. As used herein, the term "bodily orifice" refers to a duct of the cochlea, a surgical incision within the patient, or any other location within the patient. For illustrative purposes only, it will be assumed in the examples given herein that the bodily orifice refers to a duct of the cochlea.

In some examples, an insertion tool may include a stylet assembly having a stylet configured to at least partially be inserted into a lumen of the electrode array, a slide assembly configured to at least partially house the stylet assembly, and a handle assembly configured to engage at least a portion of the slide assembly. The slide assembly may be configured to selectively disengage from the handle assembly. The stylet assembly may be configured to selectively disengage from the slide assembly while the stylet is still inserted into the lumen of the electrode array. In this manner, as will be described in more detail below, the electrode array may be loaded onto the insertion tool and successfully implanted within a bodily orifice. The stylet assembly may also be disengaged from the rest of the insertion tool to allow the manual insertion of the electrode array into the bodily orifice using only the stylet assembly.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
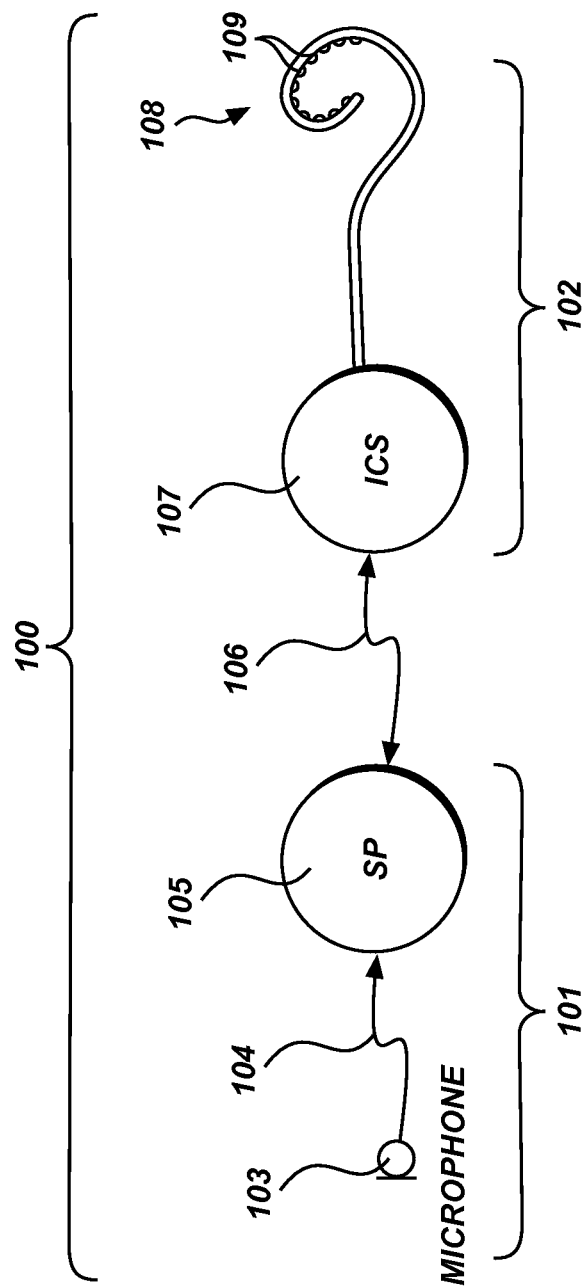
FIG. 1 illustrates an exemplary cochlear implant system according to principles described herein.

FIG. 1 illustrates an exemplary cochlear implant system 100 that may be used in accordance with the present systems and methods. Exemplary cochlear implant systems suitable for use as described herein include, but are not limited to, those disclosed in U.S. Pat. Nos. 6,219,580; 6,272,382; and 6,308,101, all of which are incorporated herein by reference in their respective entireties.

The cochlear implant system 100 of FIG. 1 includes a sound processor portion 101 and a cochlear stimulation portion 102. The sound processor portion 101 may include a microphone 103, a sound processor (SP) 105, and/or additional components as may serve a particular application. The cochlear stimulation portion 102 may include an implantable cochlear stimulator (ICS) 107, a pre-curved electrode array 108, and/or additional components as may serve a particular application. The illustrated components within sound processor portion 101 and cochlear stimulation portion 102 will be described in more detail below.

Microphone 103 is configured to sense acoustic signals and convert the sensed signals to corresponding electrical signals. The electrical signals are sent from microphone 103 to sound processor 105 via a communication link 104. Alternatively, microphone 103 may be connected directly to, or integrated with, sound processor 105. Sound processor 105 processes these converted acoustic signals in accordance with a selected signal processing strategy to generate appropriate stimulation parameters for controlling implantable cochlear stimulator 107. These parameters may specify or define the polarity, magnitude, location (i.e., which electrode pair or electrode group receive the stimulation current), and timing (i.e., when the stimulation current is to be applied to a particular electrode pair) of the electrical stimulation pulses that are generated by implantable cochlear stimulator 107.

The pre-curved electrode array 108 of FIG. 1 is configured to be inserted within a duct of the cochlea. As shown in FIG. 1, electrode array 108 includes a multiplicity of electrodes 109, e.g., sixteen electrodes, spaced along its length. It will be understood, however, that any number of electrodes 109 may be included within electrode array 108. Electrode array 108 will be described in more detail below. One or more components within implantable cochlear stimulator 107 are configured to generate stimulation current via selected pairs or groups of individual electrodes 109 in accordance with a specified stimulation pattern defined by sound processor 105.

Implantable cochlear stimulator 107 and sound processor 105 may be electronically connected via a suitable data or communication link 106. It will be understood that the data communication link 106 may include a bi-directional communication link and/or one or more dedicated uni-directional communication links.

In some examples, sound processor 105 and microphone 103 comprise an external portion of cochlear implant system 100 and implantable cochlear stimulator 107 and electrode array 108 comprise an implantable portion of system 100 that is implanted within a patient's body. In alternative embodiments, one or more portions of sound processor 105 are included within the implantable portion of the cochlear implant system 100.

The external and implantable portions of the cochlear implant system 100 may each include one or more coils configured to transmit and receive power and/or control signals via communication link 106. For example, the external portion of cochlear implant system 100 may include an external coil (not shown) and the implantable portion of cochlear implant system 100 may include an implantable coil (not shown). The external coil and the implantable coil may be inductively coupled to each other, thereby allowing data to be transmitted therebetween. The data may include, for example, the magnitude and polarity of a sensed acoustic signal. The external coil may also transmit power from the external portion to the implantable portion of cochlear implant system 100. It will be noted that, in some embodiments, both sound processor 105 and implantable cochlear stimulator 107 may be implanted within the patient, either in the same housing or in separate housings. If sound processor 105 and implantable cochlear stimulator 107 are in the same housing, communication link 106 may be realized with a direct wire connection within such housing. If sound processor 105 and implantable cochlear stimulator 107 are in separate housings, communication link 106 may include one or more inductive links, for example.

Figure 2:
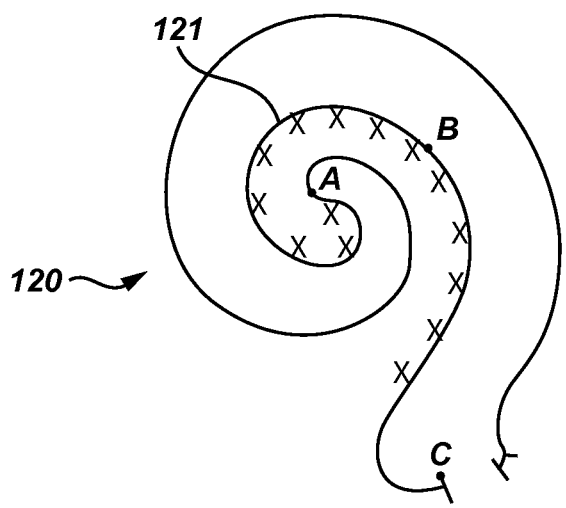
FIG. 2 illustrates a schematic structure of human cochlea according to principles described herein.

Referring to FIG. 2, there is shown a schematic structure of a human cochlea 120. The section of the cochlea 120 from point A to point B, i.e., section AB, has a spiral shape. In contrast, the section from point B to point C, i.e., section BC, is almost straight. The area of stimulation, i.e., the location of the spiral ganglion cells, is marked with X's and is separated from the duct of the cochlea 120 by the modiolar wall 121. As described previously, it is often desirable for electrodes 109 to be positioned in close proximity to the spiral ganglion cells.

Figure 3:
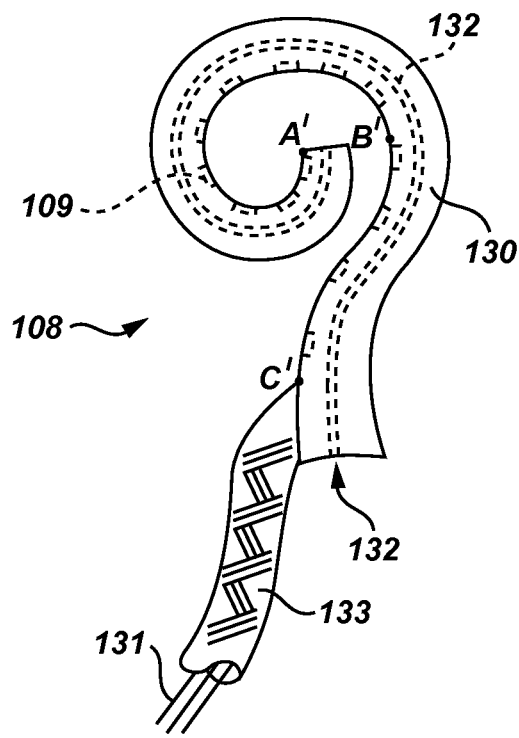
FIG. 3 illustrates an exemplary pre-curved electrode array according to principles described herein.

To facilitate proper positioning of electrodes 109, a precurved electrode array 108 is provided as shown in FIG. 3. The electrode array 108 may be substantially as shown and described in U.S. Pat. Nos. 4,819,647, 6,129,753, or 6,604,283, each of which is incorporated herein by reference in its respective entirety.

As shown in FIG. 3, pre-curved array 108 has the same general curvature as that of the cochlea 120. In some examples, pre-curved array 108 includes an elongate flexible carrier 130 having an array of electrode contacts 109 connected to corresponding insulated wires 131. Elongate flexible carrier 130 may be made out of any suitable material such as, but not limited to, silicone rubber or plastic, and has a hole or lumen 132 passing therethrough. In some examples, carrier 130 is constructed so as to have a built-in bias or memory force which forces carrier 130 to naturally assume the spiral or curved shape shown in FIG. 3. In addition, the material of the carrier 130 may be configured to allow carrier 130 to be straightened when loaded on a stylet. Once inserted within the duct of the cochlea 120, the memory force of carrier 130 forces carrier 130 to return to the desired curvature, e.g., as shown in FIG. 3.

As shown in FIG. 3, wires 131 exit carrier 130 near a proximal end thereof and form a cable 133 that connects with implantable cochlear stimulator 107. Implantable cochlear stimulator 107 is thus able to make electrical connection with each of the electrode contacts 109 through one or more of wires 131.

In some examples, the electrode contacts 109 of array 108 are configured to be positioned along the medial electrode wall following the line between points A', B' and C'. This line, as shown in FIG. 3, is along a portion of the curve or spiral that is generally concave.

As mentioned, pre-curved electrode array 108 often has to be loaded onto a stylet before it can be implanted within a duct of the cochlea. In the examples given herein, the stylet is coupled to or a part of an insertion tool. However, it will be recognized that a stand-alone stylet may alternatively be used in connection with the systems and methods described herein.

Figure 4:
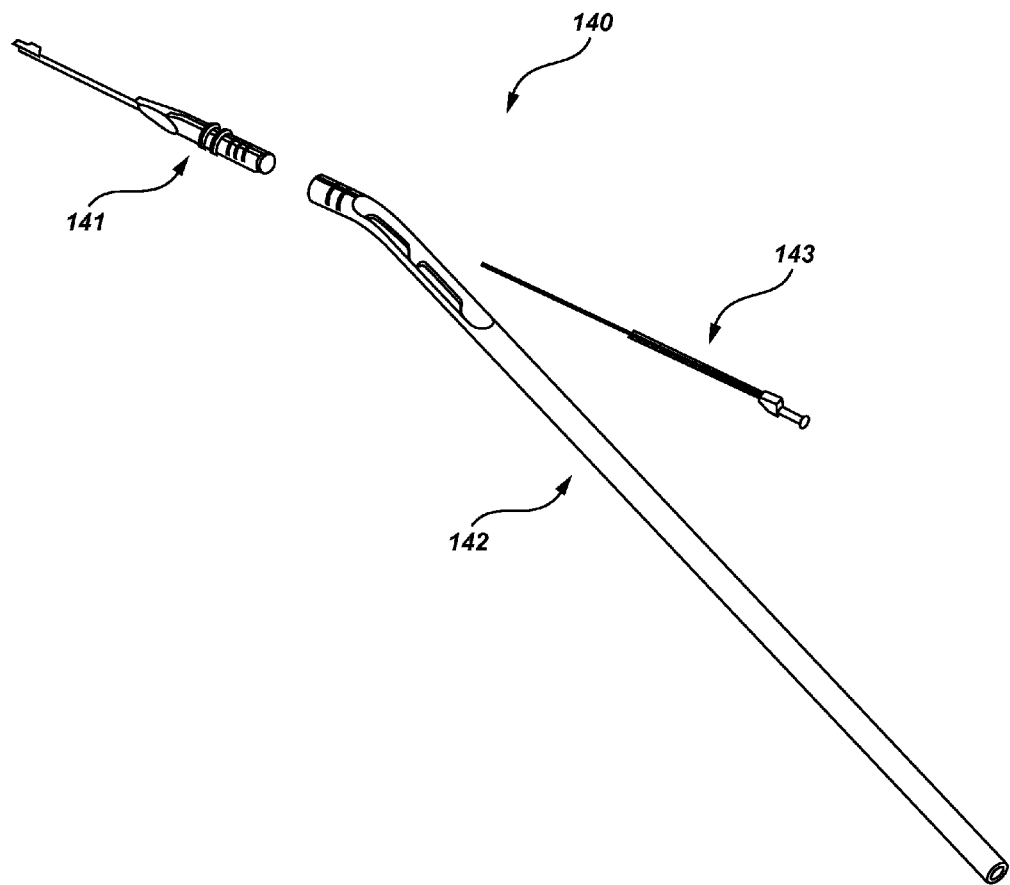
FIG. 4 is a perspective exploded view of an exemplary insertion tool that may be used to insert a pre-curved electrode array into a duct of the cochlea according to principles described herein.

Referring now to FIG. 4, an exploded view of an exemplary insertion tool 140 configured to facilitate insertion of electrode array 108 into a bodily orifice is shown. For example, the insertion tool 140 shown in FIG. 4 may be used to insert electrode array 108 into a duct of a cochlea.

As shown in FIG. 4, the exemplary insertion tool 140 may include a slide assembly 141, a handle assembly 142, and a stylet assembly 143. These components will each be described in more detail below. It will be recognized that the insertion tool 140 may include additional or alternative components as may serve a particular application.

Figure 5A:
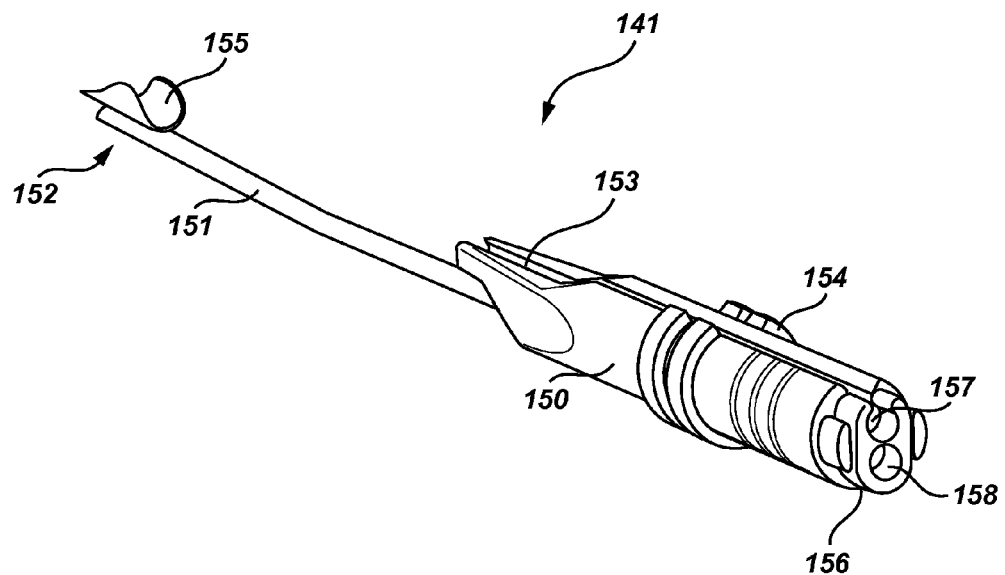
FIG. 5A is a perspective view of a slide assembly of the exemplary insertion tool of FIG. 4 according to principles described herein.
Figure 5B:
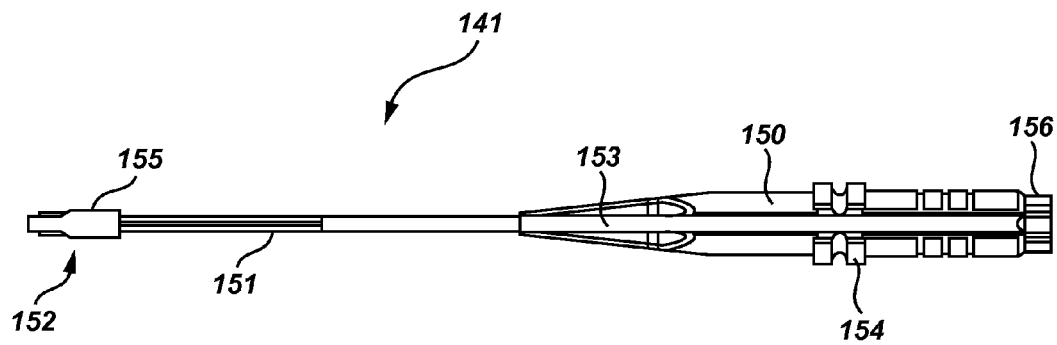
FIG. 5B is a top view of the slide assembly shown in FIG. 5A, according to principles described herein.

Referring now to FIGS. 5A and 5B, the slide assembly 141 of the exemplary insertion tool 140 is shown. FIG. 5A shows a perspective view of the slide assembly 141 and FIG. 5B shows a top view of the slide assembly 141.

Slide assembly 141 may include a main body 150 at least partially surrounding a guiding member 151. As shown in FIGS. 5A-5B, a distal portion 152 of guiding member 151 is not surrounded by main body 150 and extends distally from main body 150.

As shown in FIGS. 5A-5B, main body 150 may include a top groove 153 extending therethrough. This groove 153 may include an opening configured to receive at least a portion of stylet assembly 143, as will be explained in more detail below.

In some examples, the main body 150 of the slide assembly 141 may be configured to removably couple to handle assembly 142. To this end, a proximal portion of the main body 150 may dimensioned so as to fit within a corresponding receptacle of the handle assembly 142. One or more protruding members 154 may be coupled to or a part of main body 150 and configured to prevent handle assembly 142 from engaging too much of the main body 150 of slide assembly 141.

As shown in FIGS. 5A-5B, the distal portion 152 of the guiding member 151 may include a cradle member 155. As will be described in more detail below, cradle member 155 may be configured to receive electrode array 108.

In some examples, guiding member 151 may further include a docking member 156 coupled to a proximal portion thereof. Docking member 156 may be configured to facilitate coupling of stylet assembly 143 to slide assembly 141.

As shown in FIG. 5A, docking member 156 may include first and second orifices 157 and 158 configured to receive corresponding members of stylet assembly 143. The first orifice 157 of docking member 156 may be in communication with the groove 153 of main body 150. In this manner, as will be described in more detail below, at least a portion of stylet assembly 143 may be configured to pass through orifice 157 into groove 153.

The second orifice 158 shown in FIG. 5A may be configured to receive a corresponding locking member that is a part of stylet assembly 143. In this manner, as will be described in more detail below, stylet assembly 143 may be anchored to slide assembly 141. It will be recognized that docking member 156 may include additional or alternative receiving members as may serve a particular application.

In some examples, guiding member 151 may be slidably engaged by main body 150. Hence, force exerted upon docking member 156 may be configured to cause guiding member 151 to move along a central axis of main body 150 of slide assembly 141 in the direction of that force. In this manner, guiding member 151 may be at least partially retracted from main body 150 by pulling on docking member 156 in a proximal direction and reinserted at least partially within main body 150 by pushing docking member 156 in a distal direction. Such axial movement of guiding member 151 may facilitate loading and unloading of an electrode array 108 onto stylet assembly 143, as will be described in more detail below.

Slide assembly 141 may be made out of any suitable material with sufficient stiffness so as to facilitate entry into the cochlea or other bodily orifices as may serve a particular application. For example, the slide assembly 141 may be made out of a surgical grade steel, other metals, a metal alloy, plastic, and/or any other suitable material as serves a particular application.

Figure 6A:
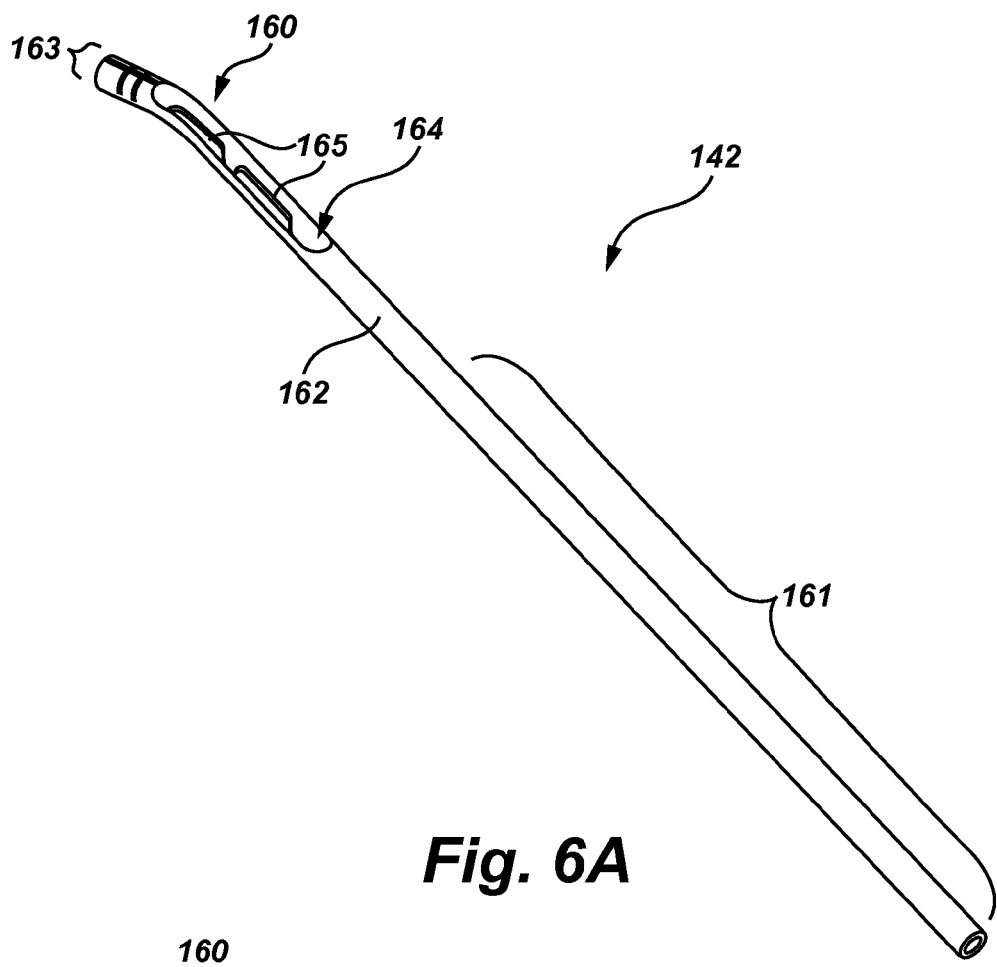
FIG. 6A is a perspective view of a handle assembly of the exemplary insertion tool of FIG. 4 according to principles described herein.
Figure 6B:
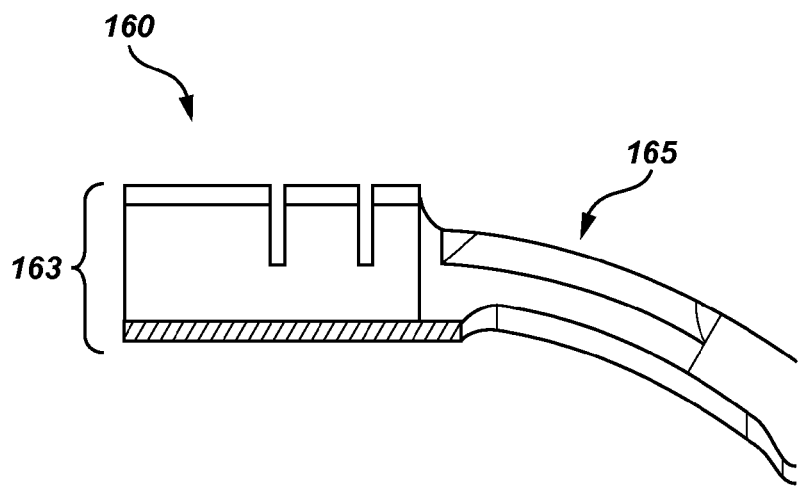
FIG. 6B is a cutaway side view of a portion of the handle assembly shown in FIG. 6A according to principles described herein.

Referring now to FIGS. 6A-6B, the handle assembly 142 of the exemplary insertion tool 140 is shown. FIG. 6A shows a perspective view of the handle assembly 142 and FIG. 6B shows a cross-sectional side view of a distal portion 160 of the handle assembly 142.

As shown in FIG. 6A, handle assembly 142 may include a proximal portion 161 and a distal portion 160. In some examples, as shown in FIG. 6A, proximal portion 161 may extend at a bent angle from distal portion 160 to facilitate a more convenient handling or holding of handle assembly 142.

In some examples, handle assembly 142 may be generally tubular in shape. However, it will be recognized that handle assembly 142 may have any other suitable shape configured to facilitate handling thereof by a clinician or other user. Moreover, handle assembly 142 may be made out of any suitable material as may serve a particular application. Examples of suitable materials out of which handle assembly 142 may be fabricated include, but are not limited to, surgical grade steel, other metals, polysulfone, other composite materials, plastics, and combinations thereof.

As shown in FIGS. 6A-6B, a receptacle 163 may be included as part of distal portion 160. Receptacle 163 may be dimensioned to mate with the proximal portion of the main body 150 of the slide assembly 141, thereby allowing handle assembly 142 to be removably coupled to slide assembly 141.

As shown in FIG. 6A, handle assembly 142 may include an inner bore 164 extending at least partially therethrough. Handle assembly 142 may also include one or more openings 165 configured to provide access to inner bore 164. Openings 165 may be used to facilitate user access to stylet assembly 143 and/or slide assembly 141 after they have been coupled to handle assembly 142.

Figures 7A, 7B:
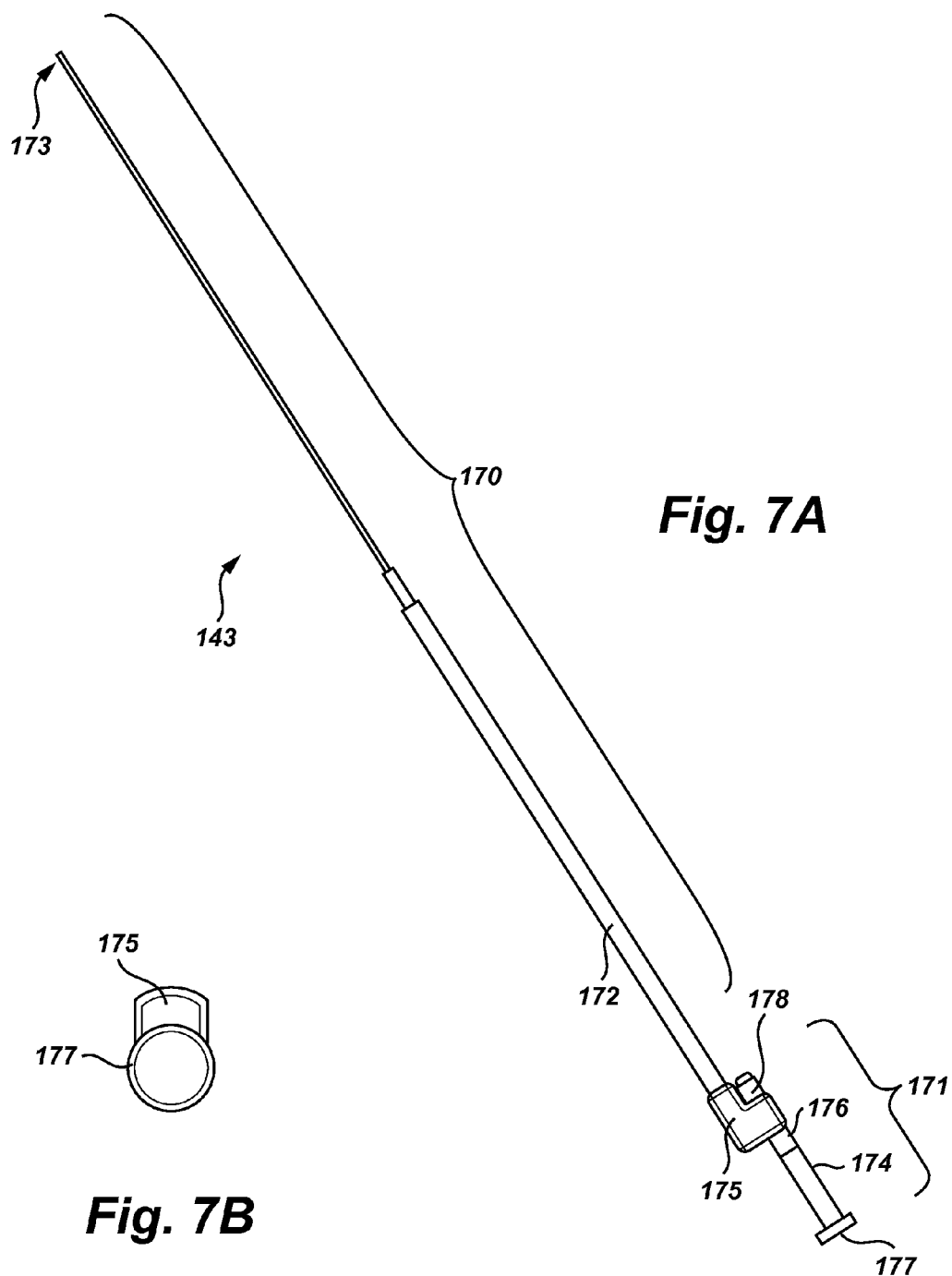
FIG. 7A is a side view of a stylet assembly of the exemplary insertion tool of FIG. 4 according to principles described herein.
FIG. 7B is a front view of the stylet assembly shown in FIG. 7A according to principles described herein.

Referring now to FIGS. 7A-7B, the stylet assembly 143 of the exemplary insertion tool 140 is shown. FIG. 7A shows a side view of the stylet assembly 143, and FIG. 7B shows a front view of a proximal end of the stylet assembly 143.

Stylet assembly 143 may include a stylet 170 coupled to a locking member 171. In some examples, stylet 170 and locking member 171 are integrated into a single component. Alternatively, stylet 170 may be removably coupled to locking member 171.

In some examples, stylet 170 may include a substantially cylindrical body 172 that tapers to a distal tip 173. Stylet 170 may be configured to be inserted at least partially within the lumen 132 of an electrode array 108 such that the electrode array 108 is maintained substantially straight during insertion into a bodily orifice. In some examples, at least a portion of stylet 170 may be coated in a synthetic polymer, such as polytetrafluoroethylene (PTFE), or any other suitable material.

Stylet 170 may be made out of any suitable material with sufficient stiffness so as to facilitate entry into the cochlea or other bodily orifices as may serve a particular application. For example, stylet 170 may be made out of a surgical grade steel, other metals, a metal alloy, plastic, and/or any other suitable material as serves a particular application.

As will be described in more detail below, the locking member 171 of the stylet assembly 143 may be configured to mate with the docking member 156 of the slide assembly 141. As shown in FIGS. 7A-7B, locking member 171 may include a locking pin 174 coupled to a pivot joint 175. However, it will be recognized that the locking member 171 may additionally or alternatively include any other component as may serve a particular application.

As shown in FIGS. 7A-7B, locking pin 174 may include a portion 176 that may be configured to couple to a complementary circular recess in a pivot joint 175, which may also be coupled to stylet 170. The coupling of locking pin 174 to pivot joint 175 may be such that locking pin 174 may rotate irrespective of any motion or lack thereof by pivot joint 175. Moreover, as shown in FIGS. 7A-7B, portions of locking pin 174 having a larger diameter than portion 176 may serve as mechanical stops configured to prevent excessive movement by locking pin 174 along or parallel to an axis defined by its length, including movements that may remove locking pin 174 from pivot joint 175.

In some examples, locking pin 174 may further include a head 177 at one end and a distal tip 178 at another end. Distal tip 178 may be configured to fit within a corresponding orifice 158 in slide assembly 141. However, when desired, the stylet assembly 143 may be selectively disengaged from the slide assembly 141 by removing the locking member 171 from the corresponding orifice 158 in the slide assembly 141 and pulling the stylet assembly 143 up through the groove 153 in the main body 150 of the slide assembly 141, as will be shown in more detail below.

Figure 8:
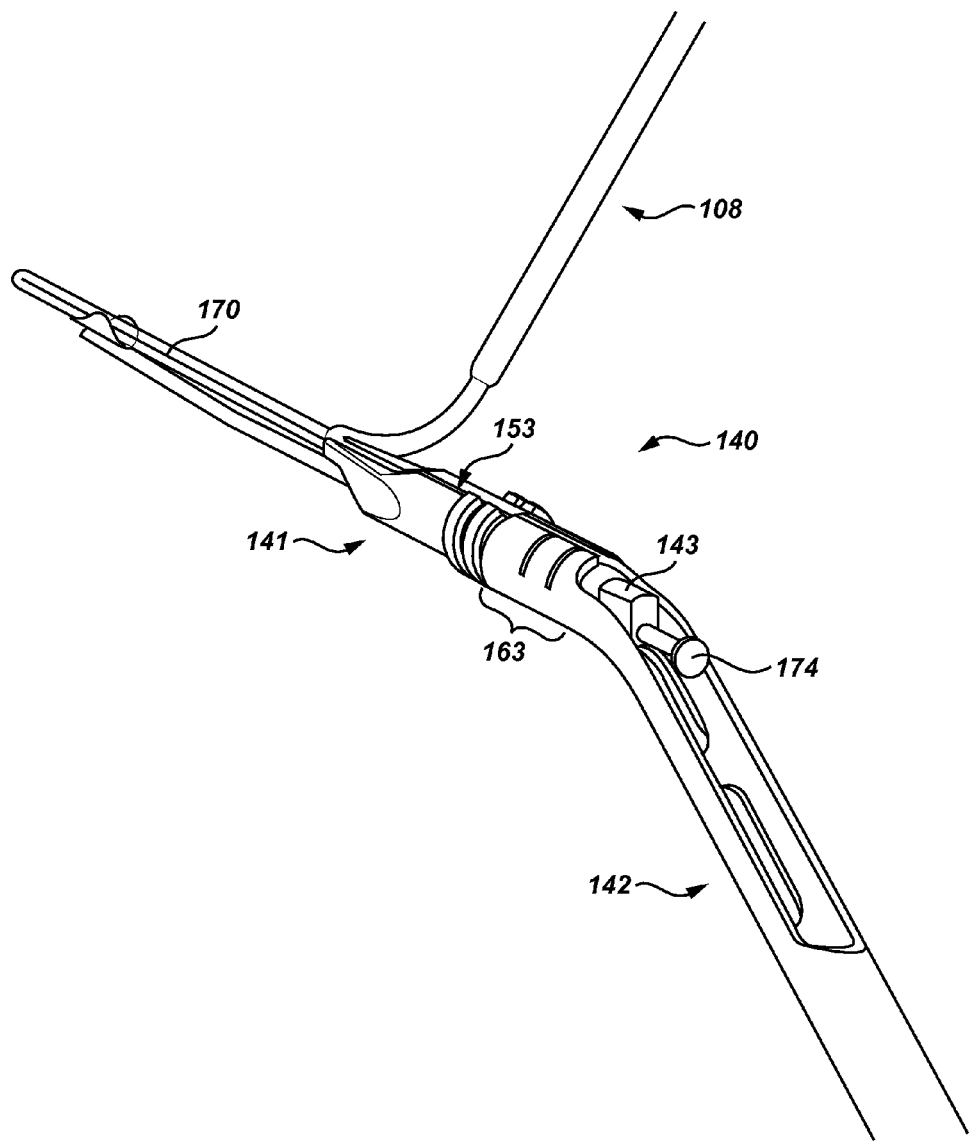
FIG. 8 is a perspective view of an exemplary insertion tool having an electrode array loaded onto a stylet assembly according to principles described herein.

Referring now to FIG. 8, a perspective view of an exemplary insertion tool 140 with an electrode array 108 loaded onto the stylet 170 of the stylet assembly 143 is shown. As shown in FIG. 8, stylet assembly 143 has been inserted within groove 153 of the slide assembly 141, which in turn, has been coupled to handle assembly 142 at receptacle 163. A user may then use handle assembly 142 to guide the loaded electrode array 108 into a bodily orifice.

As described above, stylet 170 may be inserted within the pre-curved electrode array 108 such that at least a portion of the electrode array 108 is maintained substantially straight. In this manner, the electrode array 108 may be more accurately inserted into the bodily orifice. In some examples, after electrode array 108 has been satisfactorily inserted into the bodily orifice, stylet assembly 143 may be pulled out of or otherwise removed from electrode array 108 such that electrode array 108 reassumes its pre-curved shape within the bodily orifice.

Figure 9:
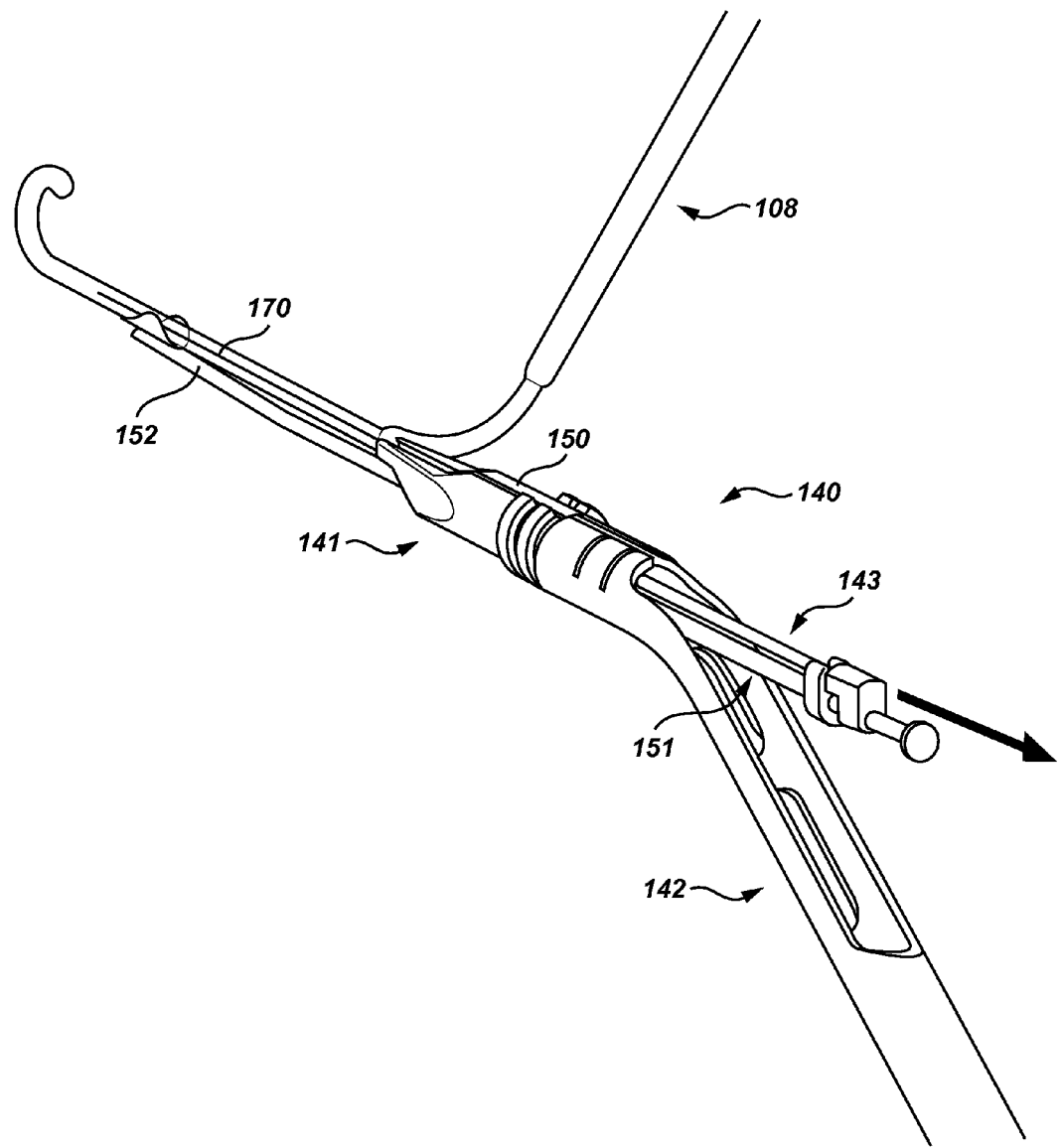
FIG. 9 illustrates the removal of a stylet assembly from an electrode array using the exemplary insertion tool shown in FIG. 8 according to principles described herein.

FIG. 9 shows the insertion tool 140 of FIG. 8 after stylet 170 has been partially removed from electrode array 108. As shown in FIG. 9, removal of the stylet 170 from the electrode array 108 may cause the electrode array 108 to reassume its pre-curved shape. In some examples, removal of stylet 170 from electrode array 108 may be facilitated by pulling stylet assembly 143 in a direction indicated by the arrow shown in FIG. 9. The force effected by pulling stylet assembly 143 may cause guiding member 151 of slide assembly 141 to proximally pass through the main body 150 of slide assembly 141 such that the distal portion 152 of guiding member 151 and stylet assembly 143 are retracted.

As stylet assembly 143 is retracted, stylet 170 is removed from lumen 132 of electrode array 108. To facilitate removal of stylet 170 from electrode array 108, electrode array 108 may be maintained substantially stationary as stylet 170 retracts.

In some examples, it may be desirable to implant the electrode array 108 within a bodily orifice using only stylet assembly 143. FIGS. 10-14 illustrate an exemplary method of disengaging the stylet assembly 143 from the slide assembly 141 and the handle assembly 142 of the exemplary insertion tool 140. In some examples, stylet assembly 142 may be disengaged from slide assembly 141 while stylet 170 is still inserted into the lumen of electrode array 108. In this manner, a physician may use the stylet assembly 142 by itself to insert electrode array 108 into a bodily orifice (e.g., a duct within the cochlea) without having to remove the electrode array 108 from the stylet 170. It will be recognized that the steps illustrated in FIGS. 10-14 are merely exemplary and that they may be reordered, modified, or otherwise varied as may serve a particular application.

Figure 10:
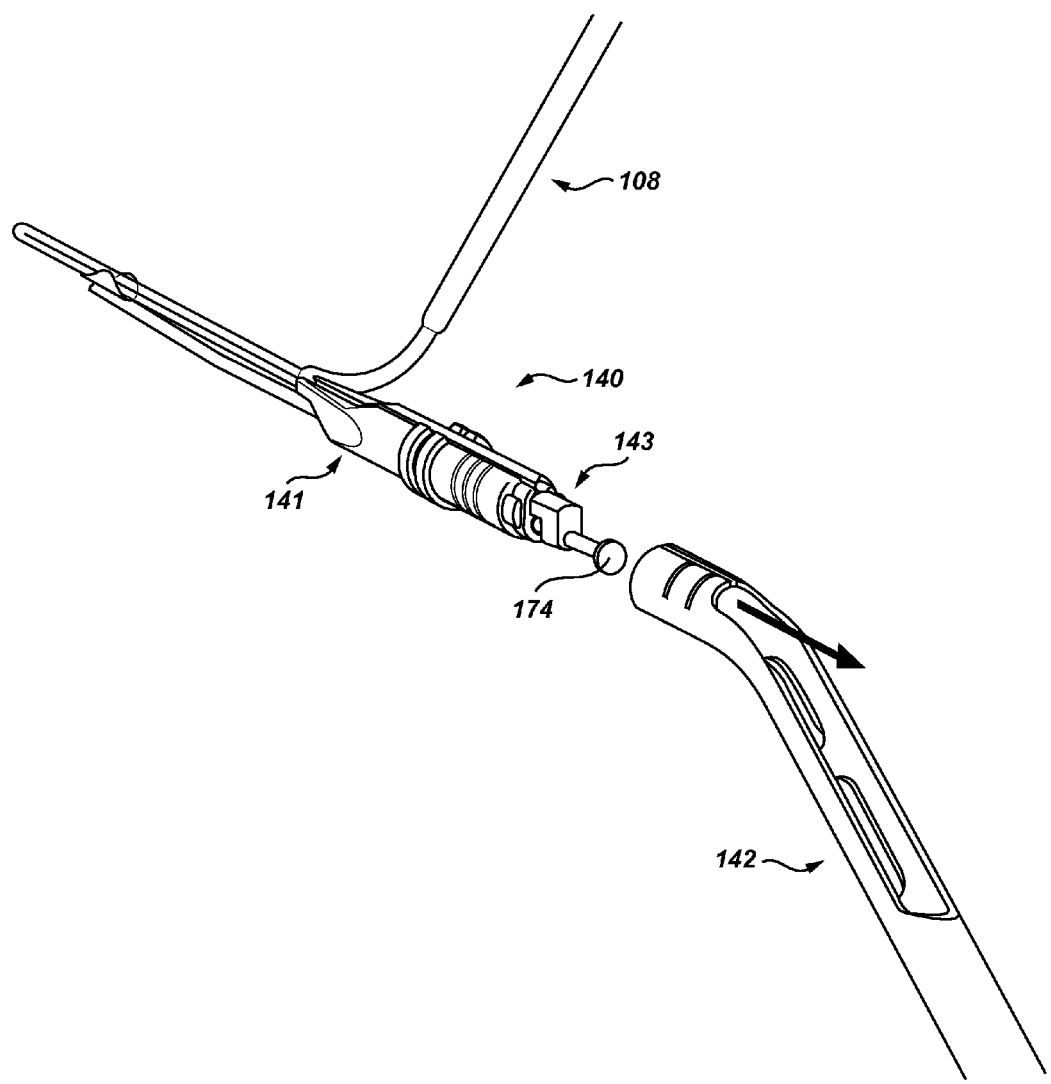
FIGS. 10-14 illustrate an exemplary method of disengaging a stylet assembly from an insertion tool according to principles described herein.

As shown in FIG. 10, the handle assembly 142 may be first disengaged from the slide assembly 141. In some examples, a force may be exerted on the handle assembly 142 in the direction of the arrow shown in FIG. 10 such that the handle assembly 142 disengages from the slide assembly 141.

Figure 11:
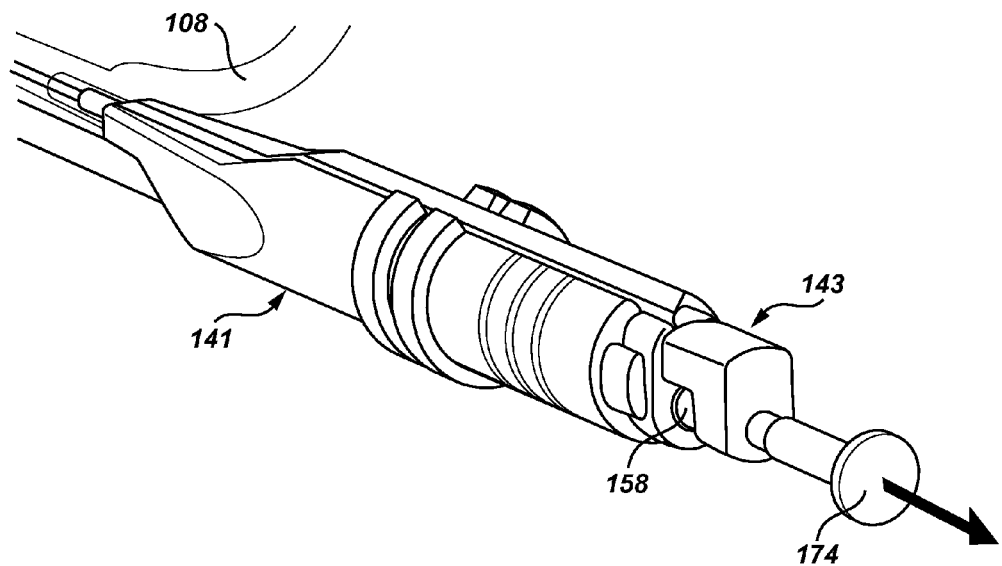
Figure 12:
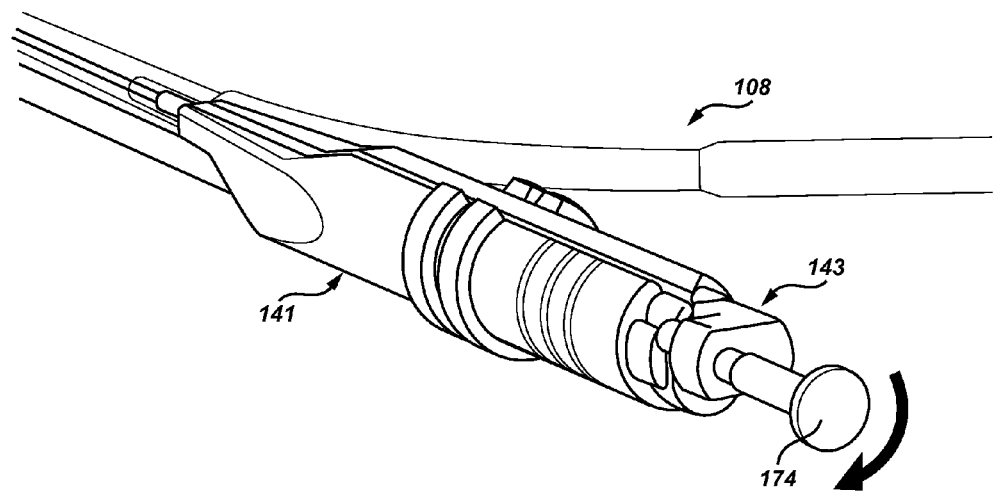
Figure 13:
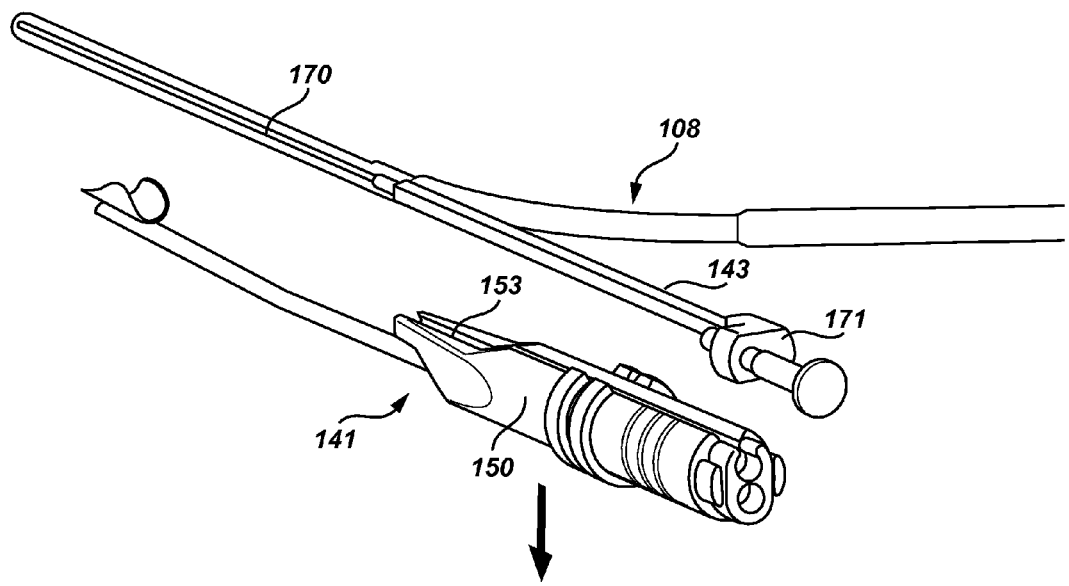

FIGS. 11-13 illustrate exemplary steps of disengaging stylet assembly 143 from slide assembly 141. As shown in FIG. 11, locking pin 174 may be pulled in the direction of the arrow to disengage locking pin 174 from the corresponding orifice 158 in slide assembly 141. With locking pin 174 thus removed, stylet assembly 143 is no longer locked in a fixed position with respect to slide assembly 141.

As shown in FIG. 12, stylet assembly 143 may then be rotated a certain amount by rotating the disengaged locking member 171 in a direction indicated by the arrow. This rotation may optimally position stylet assembly 143 for removal from slide assembly 141. The amount of rotation may vary as may serve a particular application. To illustrate, in the example of FIG. 12, stylet assembly 143 has been rotated approximately 90 degrees. In some alternative embodiments, stylet assembly 143 may be disengaged from slide assembly 141 without being rotated.

Stylet assembly 143 may then be disengaged from slide assembly 141, as shown in FIG. 13. In some examples, stylet assembly 143 may be disengaged from slide assembly 141 by removing stylet assembly 143 from slide assembly 141 via open groove 153. As shown in FIG. 13, stylet 170 is still inserted into a lumen of electrode array 108. This is advantageous in that a surgeon or other user may quickly switch between using insertion tool 140 and a stand-alone stylet assembly 143 to insert electrode array 108 into a bodily orifice.

Figure 14:
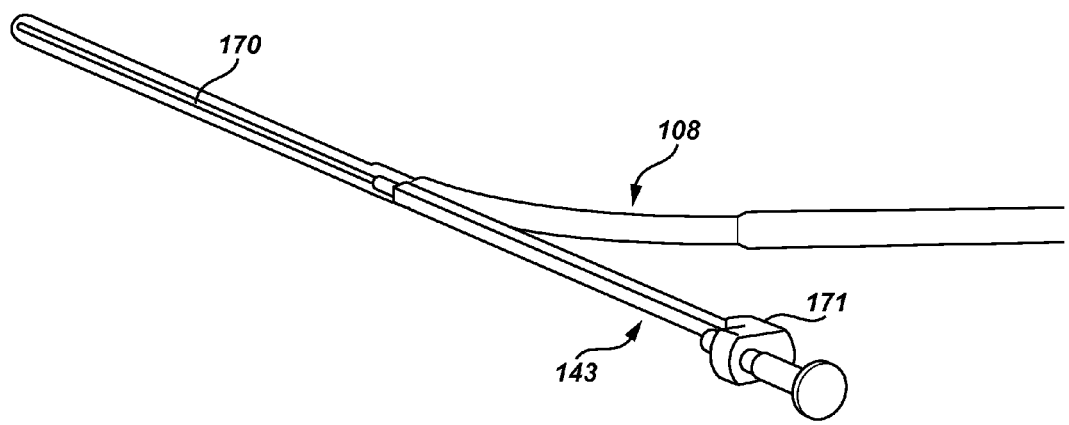

FIG. 14 shows stylet assembly 143 after it has been disengaged from slide assembly 141. A practitioner may use the disengaged stylet assembly 143 to insert the electrode array 108 into a bodily orifice.

Figure 15:
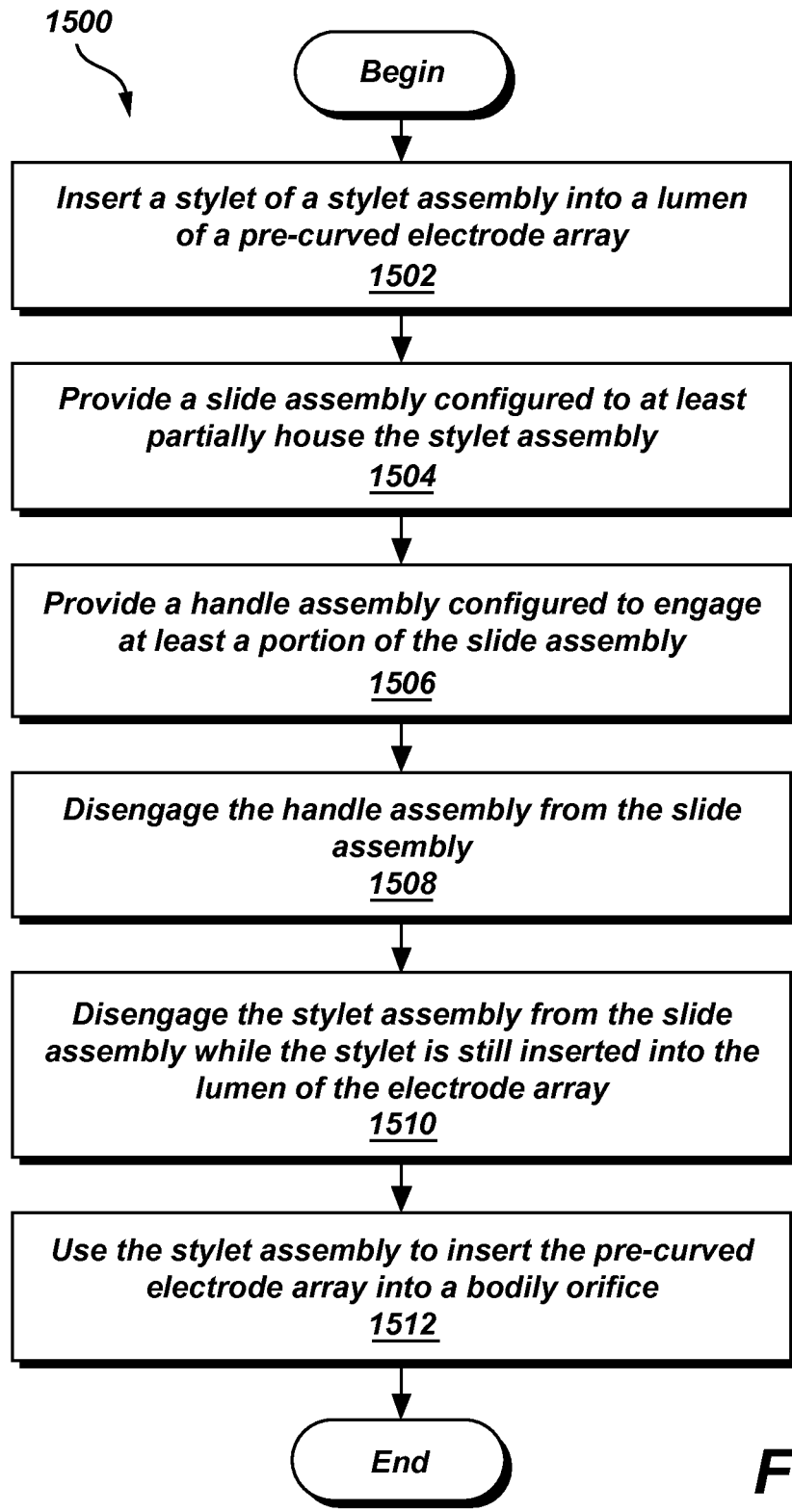
FIG. 15 illustrates an exemplary method of inserting a pre-curved electrode array into a bodily orifice.

FIG. 15 illustrates an exemplary method 1500 of inserting a pre-curved electrode array into a bodily orifice. While FIG. 15 illustrates exemplary steps according to one embodiment, other embodiments may omit, add to, reorder, and/or modify any of the steps shown in FIG. 15.

In step 1502, a stylet of a stylet assembly is inserted into a lumen of a pre-curved electrode array. The stylet may be inserted in any of the ways described herein.

In step 1504, a slide assembly configured to at least partially house the stylet assembly is provided. The slide assembly may include or be similar to slide assembly 141 described herein.

In step 1506, a handle assembly configured to engage at least a portion of the slide assembly is provided. The handle assembly may include or be similar to handle assembly 142 described herein.

In step 1508, the handle assembly is disengaged from the slide assembly. The handle assembly may be disengaged from the slide assembly in any of the ways described herein.

In step 1510, the stylet assembly is disengaged from the slide assembly while the stylet is still inserted into the lumen of the electrode array. The stylet assembly may be disengaged from the slide assembly in any of the ways described herein.

In step 1512, the stylet assembly is used to insert the pre-curved electrode array into the bodily orifice. For example, the stylet assembly may be used to insert the pre-curved electrode array into a duct of the cochlea.

Hence, an exemplary insertion tool for facilitating insertion of an electrode array into a bodily orifice includes a stylet assembly having a stylet configured to be inserted into a lumen of the electrode array, a slide assembly configured to at least partially house the stylet assembly, and a handle assembly configured to engage at least a portion of the slide assembly. The slide assembly may be configured to selectively disengage from the handle assembly. The stylet assembly may be configured to selectively disengage from the slide assembly while the stylet is still inserted into the lumen of the electrode array.

In some embodiments, slide assembly includes a main body configured to at least partially house the stylet assembly and a guiding member configured to receive and guide the electrode array to the bodily orifice, wherein the main body at least partially surrounds the guiding member.

In some embodiments, the guiding member is configured to at least partially retract through the main body.

In some embodiments, the main body includes a top groove configured to selectively receive the stylet assembly.

In some embodiments, the stylet assembly further includes a locking member configured to engage a corresponding orifice in the slide assembly.

In some embodiments, the stylet assembly is selectively disengaged from the slide assembly by selectively disengaging the locking member from the corresponding orifice.

In some embodiments, the electrode array includes a pre-curved shape.

In some embodiments, at least one of the slide assembly, the handle assembly, and the stylet assembly is fabricated out of a material including at least one or more of a surgical grade steel, a metal, polysulfone, a composite material, and a plastic.

An exemplary system includes a pre-curved electrode array configured to provide electrical stimulation to one or more stimulation sites within a duct of a cochlea and an insertion tool configured to insert the electrode array into the duct of the cochlea. The insertion tool includes a stylet assembly including a stylet configured to be inserted into a lumen of the electrode array, a slide assembly configured to at least partially house the stylet assembly, and a handle assembly configured to engage at least a portion of the slide assembly. The slide assembly may be configured to selectively disengage from the handle assembly. The stylet assembly may be configured to selectively disengage from the slide assembly while the stylet is still inserted into the lumen of the electrode array.

An exemplary method includes inserting a pre-curved electrode array into a bodily orifice include inserting a stylet of a stylet assembly into a lumen of a pre-curved electrode array, providing a slide assembly configured to at least partially house the stylet assembly, providing a handle assembly configured to engage at least a portion of the slide assembly, disengaging the handle assembly from the slide assembly, disengaging the stylet assembly from the slide assembly while the stylet is still inserted into the lumen of the pre-curved electrode array, and using the stylet assembly to insert the pre-curved electrode array into the bodily orifice.

In some embodiments, the disengaging of the stylet assembly from the slide assembly includes disengaging a locking member in the stylet assembly from a corresponding orifice in the slide assembly.

In some embodiments, the disengaging of the handle assembly from the slide assembly includes removing at least a portion of the slide assembly from an inner bore of the handle assembly.

The preceding description has been presented only to illustrate and describe embodiments of the invention. It is not intended to be exhaustive or to limit the invention to any precise form disclosed. Many modifications and variations are possible in light of the above teaching.

What is claimed is:

1. An insertion tool configured to facilitate insertion of an electrode array into a bodily orifice, said insertion tool comprising:
    a stylet assembly comprising
        a stylet configured to be inserted into a lumen of said electrode array, and
        a locking member coupled to a proximal end of said stylet, said locking member comprising a pivot joint and a locking pin disposed within a recess of said pivot joint;
    a slide assembly comprising
        a docking member comprising an orifice and configured to anchor said stylet assembly to said slide assembly by receiving said locking pin of said locking member within said orifice, and
        a main body,
        wherein said slide assembly is configured to at least partially house said stylet assembly within said main body; and
    a handle assembly comprising a receptacle and configured to engage at least a portion of said slide assembly by receiving said main body of said slide assembly within said receptacle;
    wherein said slide assembly is configured to be selectively and completely removed from said handle assembly in response to a force exerted on at least one of said handle assembly and said slide assembly while said main body of said slide assembly is within said receptacle, said force causing said main body of said slide assembly to completely exit from said receptacle of said handle assembly; and
    wherein said stylet assembly, including said stylet and said locking member coupled to said proximal end of said stylet, is configured to selectively disengage from said slide assembly, while said stylet is still inserted into said lumen of said electrode array and while said locking member is coupled to said stylet, in response to a removal by a user of said locking pin from said orifice and a rotation by said user of said locking member after said locking pin is removed from said orifice.

2. The insertion tool of claim 1, wherein said slide assembly comprises:
    a guiding member configured to receive and guide said electrode array to said bodily orifice;
    wherein said main body at least partially surrounds said guiding member.

3. The insertion tool of claim 2, wherein said guiding member is configured to at least partially retract through said main body.

4. The insertion tool of claim 1, wherein said main body comprises a top groove configured to selectively receive said stylet assembly.

5. The insertion tool of claim 1, wherein said electrode array comprises a pre-curved shape.

6. The insertion tool of claim 1, wherein at least one of said slide assembly, said handle assembly, and said stylet assembly is fabricated out of a material comprising at least one or more of a surgical grade steel, a metal, polysulfone, a composite material, and a plastic.

7. The insertion tool of claim 1, wherein said stylet assembly is configured to be selectively disengaged from said slide assembly by being completely removed from said slide assembly.

8. A system, comprising:
    a pre-curved electrode array configured to provide electrical stimulation to one or more stimulation sites within a duct of a cochlea; and
    an insertion tool configured to insert said electrode array into said duct of said cochlea, said insertion tool comprising
        a stylet assembly comprising
            a stylet configured to be inserted into a lumen of said electrode array, and
            a locking member coupled to a proximal end of said stylet, said locking member comprising a pivot joint and a locking pin disposed within a recess of said pivot joint,
        a slide assembly comprising
            a docking member comprising an orifice and configured to anchor said stylet assembly to said slide assembly by receiving said locking pin of said locking member within said orifice, and
            a main body,
            wherein said slide assembly is configured to at least partially house said stylet assembly within said main body; and
        a handle assembly comprising a receptacle and configured to engage at least a portion of said slide assembly by receiving said main body of said slide assembly within said receptacle;
        wherein said slide assembly is configured to be selectively and completely removed from said handle assembly in response to a force exerted on at least one of said handle assembly and said slide assembly while said main body of said slide assembly is within said receptacle, said force causing said main body of said slide assembly to completely exit from said receptacle of said handle assembly; and
        wherein said stylet assembly, including said stylet and said locking member coupled to said proximal end of said stylet, is configured to selectively disengage from said slide assembly, while said stylet is still inserted into said lumen of said electrode array and while said locking member is coupled to said stylet, in response to a rotation of said locking member by a user.

9. The system of claim 8, wherein said slide assembly comprises:
   a guiding member configured to receive and guide said electrode array to said bodily orifice;
   wherein said main body at least partially surrounds said guiding member.

10. The system of claim 9, wherein said guiding member is configured to at least partially retract through said main body.

11. The system of claim 8, wherein said main body comprises a top groove configured to selectively receive said stylet assembly.

12. The system of claim 8, wherein said electrode array comprises a pre-curved shape.

13. The system of claim 8, wherein at least one of said slide assembly, said handle assembly, and said stylet assembly is fabricated out of a material comprising at least one or more of a surgical grade steel, a metal, polysulfone, a composite material, and a plastic.

14. A method of inserting a pre-curved electrode array into a bodily orifice, said method comprising:
   inserting a stylet of a stylet assembly into a lumen of a pre-curved electrode array, said stylet assembly comprising a locking member coupled to a proximal end of said stylet, said locking member comprising a pivot joint and a locking pin disposed within a recess of said pivot joint;
   providing a slide assembly comprising a main body and configured to at least partially house said stylet assembly within said main body, said slide assembly further comprising a docking member comprising an orifice and configured to anchor said stylet assembly to said slide assembly by receiving said locking pin of said stylet assembly within said orifice;
   providing a handle assembly comprising a receptacle and configured to engage at least a portion of said slide assembly by receiving said main body of said slide assembly within said receptacle;
   completely removing said handle assembly from said slide assembly by exerting a force on at least one of said handle assembly and said slide assembly while said main body of said slide assembly is within said receptacle, said force causing said main body of said slide assembly to completely exit from said receptacle of said handle assembly;
   disengaging said stylet assembly, including said stylet and said locking member coupled to said proximal end of said stylet, from said slide assembly, while said stylet is still inserted into said lumen of said pre-curved electrode array and while said locking member is coupled to said stylet, by removing said locking pin from said orifice and by rotating said locking pin subsequent to said locking member being removed from said orifice; and
   using said stylet assembly to insert said pre-curved electrode array into said bodily orifice.

15. The method of claim 14, wherein said bodily orifice comprises a duct of a cochlea.

* * * * *